United States Patent [19]

Greer et al.

[11] Patent Number: 5,538,690
[45] Date of Patent: Jul. 23, 1996

[54] AIR QUALITY INDICATOR SYSTEM FOR BREATHING AIR SUPPLIES

[76] Inventors: Garry L. Greer, 4535 Vista Grande Rd.; Jack L. Schrader, 5755 Prince Placer Rd., both of Hereford, Ariz. 85615; James A. Gideon, 1734 W. Calle Reina, Tucson, Ariz. 85705

[21] Appl. No.: 220,909

[22] Filed: Mar. 31, 1994

Related U.S. Application Data

[63] Continuation-in-part of Ser. No. 779,912, Oct. 21, 1991, abandoned.

[51] Int. Cl.$^6$ .................................................. G01J 1/48
[52] U.S. Cl. .................................. 422/86; 422/56; 422/58; 422/59; 422/88; 436/134; 436/165; 436/167; 436/169; 436/181; 137/329.3; 137/329.4; 128/202.22; 128/205.23; 128/205.24; 73/31.03; 73/863.71; 73/863.72
[58] Field of Search .................................. 436/134, 165, 436/167, 169, 181; 422/56, 58, 59, 86, 88, 60; 137/329.3, 329.4; 128/202.22, 202.27, 204.18, 205.22, 205.23, 205.24; 73/31.03, 863.71, 23.2, 863.72

[56] References Cited

U.S. PATENT DOCUMENTS

| | | | |
|---|---|---|---|
| 2,569,895 | 10/1951 | Main-Smith et al. | 436/134 X |
| 3,312,527 | 4/1967 | McConnaughey | 436/134 X |
| 3,388,975 | 6/1968 | Wallace | 436/134 X |
| 4,132,395 | 1/1979 | Fox, Jr. | 267/64.23 |
| 4,135,632 | 1/1979 | Berkel, Jr. | 414/698 |
| 4,159,304 | 6/1979 | Shono | 422/104 |
| 4,340,157 | 7/1982 | Darner | 222/211 |
| 4,389,372 | 6/1983 | Lalin | 422/88 |
| 4,459,266 | 7/1984 | Lamoreaux | 422/86 |
| 4,479,520 | 10/1984 | Holben | 141/1 |
| 4,527,587 | 7/1985 | Fairlamb | 137/329.3 |
| 4,923,806 | 5/1990 | Klodowski | 436/39 |
| 5,069,879 | 12/1991 | Leichnitz et al. | 422/86 |
| 5,071,768 | 12/1991 | Klodowski | 436/39 |
| 5,168,068 | 12/1992 | Yanagisawa et al. | 436/134 |
| 5,417,204 | 5/1995 | Moesle, Jr. | 128/205.23 |

*Primary Examiner*—Robert J. Warden
*Assistant Examiner*—Maureen M. Wallenhorst
*Attorney, Agent, or Firm*—Gregory J. Nelson

[57] ABSTRACT

An apparatus for indicating the presence of CO and oil in a compressed breathing air supply provided in a tank. An indicator contains a substance which undergoes an observable physical change when exposed to a contaminant. The indicator is activated and placed in a housing and connected to the air supply and the indicator observed. In a preferred embodiment, the indicator is a single use indicator and contains an indicating gel in a glass tube which is opened by breaking at the time of use. Appropriate reference indicia are provided so the user may visually determine the contaminant level.

6 Claims, 3 Drawing Sheets

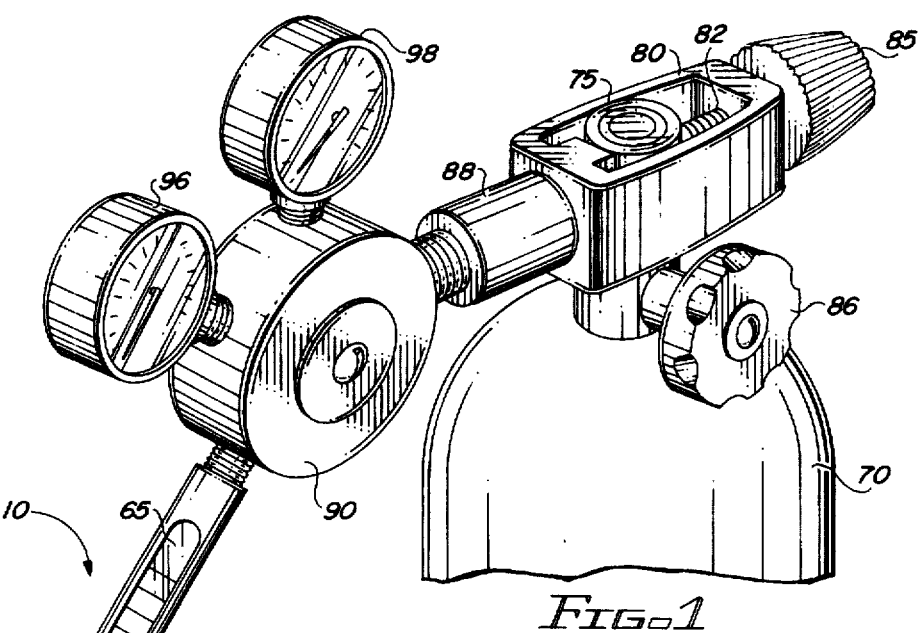
FIG. 1
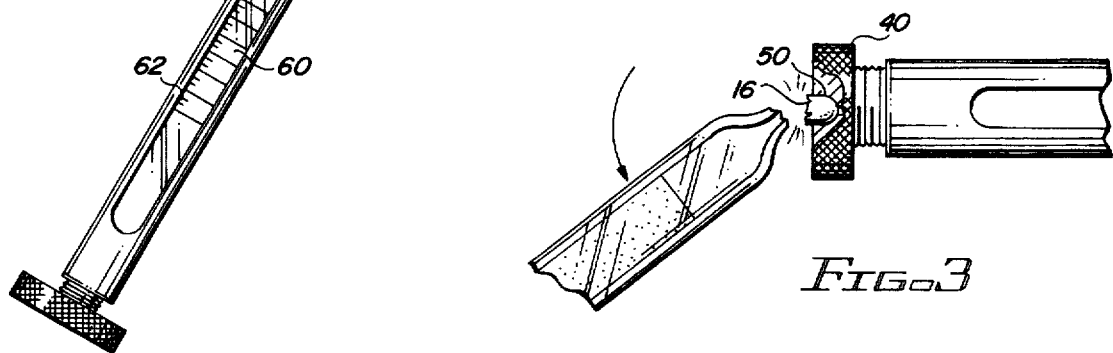
FIG. 2
FIG. 3
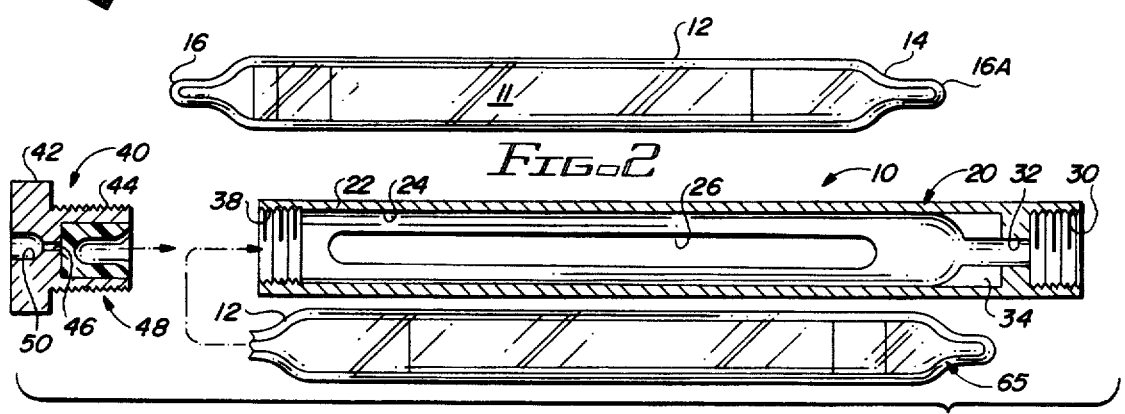
FIG. 4
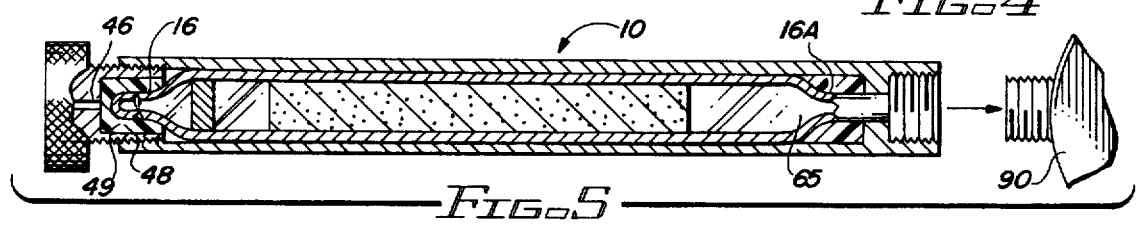
FIG. 5

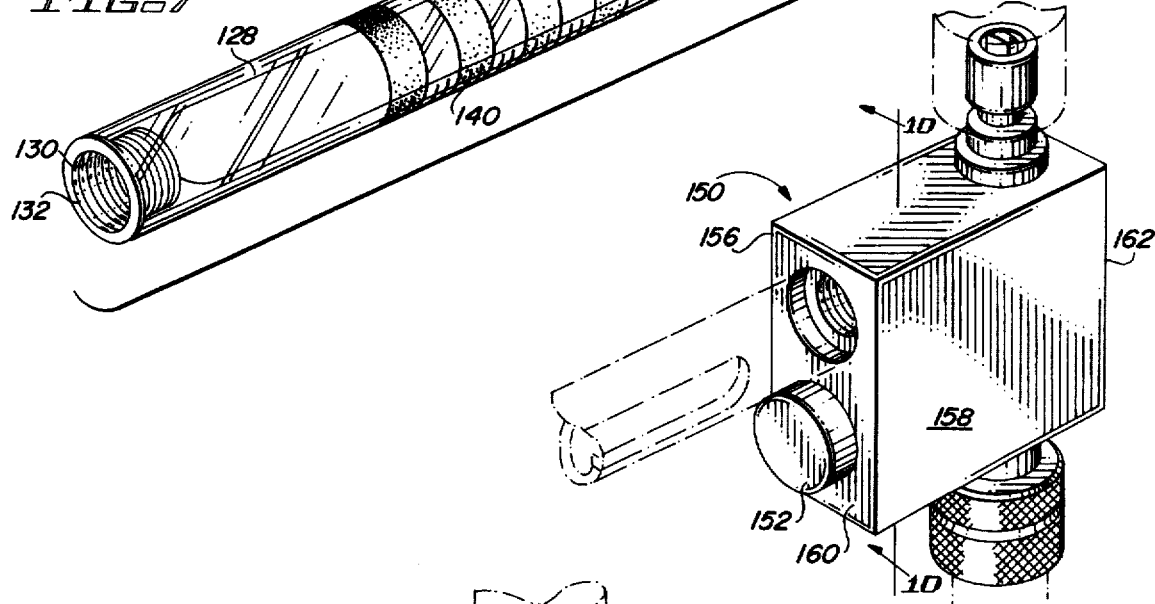

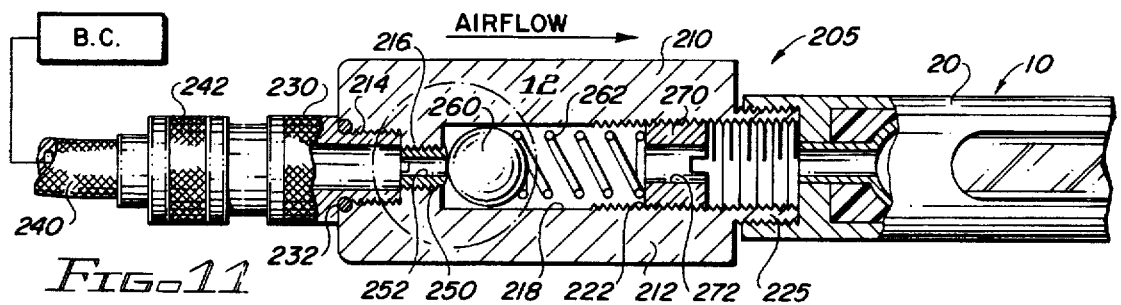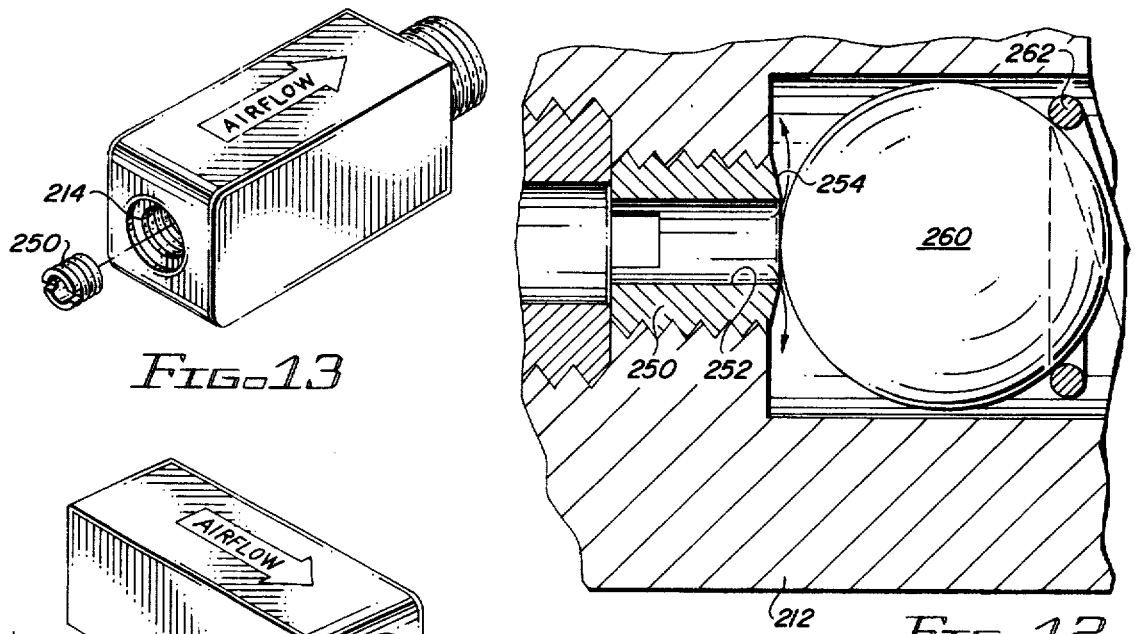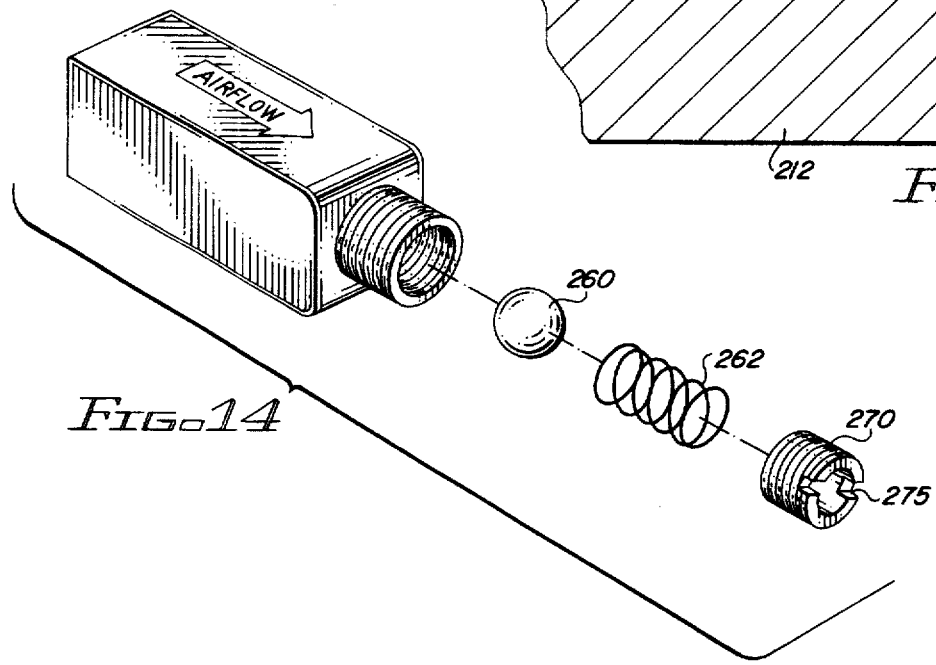

AIR QUALITY INDICATOR SYSTEM FOR BREATHING AIR SUPPLIES

This is a continuation-in-part of application Ser. No. 07/779,912, filed on Oct. 21, 1991, and now abandoned.

The present invention relates to a device for indicating the presence of toxic substances in air and more particularly concerns a colorimetric indicating device for detecting toxic substances such as carbon monoxide in compressed air supplies intended for breathing such as air contained in scuba air tanks.

Scuba diving has become an increasingly popular sport over the years with over 80,000 new divers being certified annually. As is well known, scuba divers rely on a source of compressed air contained in a tank which is supplied to the diver through a regulator system. Conventionally, the air tanks are periodically replenished with compressed air usually by means of a compressor using ambient air as the source. If the ambient air is of poor quality or if the compressor equipment is not properly operated or maintained, contaminants can find their way into the diver's air supply. Often these contaminants are in the form of oil or carbon monoxide. Excessive levels of carbon monoxide, particularly above concentrations of thirty parts per million can cause illness with the diver's having symptoms including reddish flushed lips, headaches and nausea, vomiting and mental confusion. Higher levels of carbon monoxide or long exposure to excessive levels of carbon monoxide can even cause death.

The problem of contaminants in the air supply is of particular concern to divers as at depth the increased partial pressure of oxygen can meet the body's requirements even though the blood hemoglobin is bound or "locked up" with CO. However, during ascent the total pressure will decrease as will the partial pressure of oxygen and since the body's requirements for oxygen cannot be sustained, unconsciousness may occur.

Oil contamination also presents a problem to divers. The maximum allowable amount of oil vapor in air for breathing is 5 mg/m$^3$. When breathed into the lungs, oil vapor may cause a condition known as lipid pneumonia. The irritant effect of the oil may lead to loss of pulmonary function. The *PADI Diver Manual*, pages 112 and 154, addresses the problems of a diver receiving a contaminated tank of air.

Often divers find it necessary to have their tanks replenished in remote areas of the world where regulation or concerns of compressor operators may be less stringent. The problem of having a reliable, contaminant-free source of compressed air is of concern not only to scuba divers but to others using sources of air for breathing such as firefighters and others who find it necessary to enter areas where breathing apparatus are worn. Thus, the present invention applies not only to scuba equipment but to other self contained breathing apparatus (SCBA) systems such as those used by firefighters.

As a result of the foregoing, there exists a substantial need for a simple, portable and effective personal device for indicating the presence of toxic substances in air supplies to be used for breathing. The prior art reveals that little has been done in this area.

U.S. Pat. No. 2,569,895 shows a device for the detection and/or quantitative determination of carbon monoxide in a mixture with air of other gases which device has a rubber bulb which may be squeezed to release a standard quantity of air through an indicator reagent material which is a simple or complex sulfite of palladium which reagent undergoes a change in color.

U.S. Pat. No. 4,748,930 concerns a colorimetric gas dosimeter which contains a color indicator disk on one side wall and a box-shaped, flat measuring chamber.

U.S. Pat. No. 4,882,287 relates to a process for indicating toxic substances in air that is supplied to areas such as a cab of a motor vehicle.

U.S. Pat. No. 3,507,622 relates a device for indicating the presence of contaminants in air which has a rotatable disk which causes a sample to be drawn through the indicating means to indicate the presence of contaminants in the air.

Thus, while there are various indicator substances and devices in the prior art, none are personal and portable devices adapted for use for checking compressed air sources as commonly used in scuba, self contained breathing apparatus (SCBA) and similar systems.

Accordingly, it is a principal object of the present invention to provide a simple, colorimetric indicating system for testing air supplies.

It is another object of the present invention to provide a portable device which will allow a diver and other users of compressed air for breathing to consistently and accurately check his or her individual air supply for dangerous contaminants.

It is another object of the present invention to provide a colorimetric indicating system for determining the presence of carbon monoxide and other contaminants which system utilizes a replaceable, reagent-containing colorimetric indicator tube.

It is an object of the present invention to provide a device for indicating the presence of toxic substances in air which may be easily and conveniently attachable to a tank or air supply system.

Briefly, the present invention provides a method and apparatus for indicating the presence of CO and oil in a compressed breathing air supply provided in a tank. An indicator contains a substance which undergoes an observable physical change when exposed to a contaminant. The indicator is activated and placed in a housing and connected to the air supply and the indicator observed. In a preferred embodiment, the indicator is a single use indicator and contains an indicating gel in a glass tube which is opened by breaking at the time of use. Appropriate reference indicia are provided so the user may visually determine the contaminant level.

The above and other objects of the present invention will become more apparent from the following description, claims and drawings in which:

FIG. 1 is a perspective view showing the colorimetric indicating assembly in conjunction with a pressure regulator and adaptor connecting the system to a source of compressed air;

FIG. 2 shows the replaceable indicator tube component;

FIG. 3 illustrates the end of the indicator tube and the end of the cartridge cooperating to rupture or break off the end of the tube;

FIG. 4 illustrates the assembly of the indicator tube into the cartridge;

FIG. 5 is a cross sectional view showing the indicator tube in a position within the cartridge;

FIG. 6 is a detailed view of the end of the indicator cartridge and quick-connect coupling;

FIG. 7 is a view of the end of the cartridge showing a threaded end configuration;

FIG. 8 is a perspective view illustrating another embodiment of the cartridge;

FIG. 9 is a perspective view illustrating an adaptor which may be installed in an air pressure line to which the colorimetric indicator assembly may be easily connected;

FIG. 10 is a cross-sectional view taken along line 10—10 of FIG. 9;

FIG. 11 is a view partly in section of another embodiment of the air quality indicating system of the present invention;

FIG. 12 is a detail view as indicated in FIG. 11;

FIG. 13 is a perspective view partly exploded of one end of the adaptor valve; and FIG. 14 is a perspective view of the opposite ends of the adaptor valve.

Turning to the drawings, particularly FIGS. 2–5, the basic components of the colorimetric indicator system of the present invention is shown in detail and the basic system is indicated by the numeral 10. The term "colorimetric" is used to characterize an indicator which changes color to indicate either qualitatively or quantitatively the presence of a monitored substance. In the present case, the present invention will be described with reference to monitoring the detection of carbon monoxide although it will be appreciated that other toxic substances can be monitored and measured by selecting the appropriate indicating substance or reagent.

An indicating substance 11 is contained in an elongate, hollow, transparent tube 12 which is preferably clear glass. The opposite ends of the tube each have a shoulder 14 which provides a transition to axially extending tips 16 and 16A. In the case of carbon monoxide, a suitable reagent for the detection of carbon monoxide is a simple or complex sulfite of palladium or a mixture containing the palladous and sulfite radicals deposited on a carrier such as a silica gel. A color response of the indicating substance is a function of the product of time and the concentration at any constant rate of flow. Indicating substances of this type are more fully described in the aforementioned U.S. Pat. No. 2,569,895 and in a report entitled "Rapid Determination of Small Amounts of Carbon Monoxide", by Martin Shepherd, published by the National Bureau of Standards. Other gas indicators of this general type are available in the art, such as the gas indicator tube containing synthetic amorphous silica sold by Bacharach, Inc. of Pittsburgh, Pa.

The indicator assembly includes the replaceable indicator tube 12 as described above and a cartridge 20 which receives the indicator tube during the testing procedure. The indicator tube is a single-use device and is discarded after a test for contaminants or impurities has been conducted. During the test, the indicator tube is received in the cartridge 20 which cartridge has an elongate, cylindrical housing 22 defining an axially extending chamber 24 having a major diameter adapted to snugly receive the tube 12. An elongate viewing slot or window 26 extends in the surface of the housing to expose a substantial portion of the contained indicator tube. The inlet end of the cartridge is provided with internal threads 30 so the tube may be connected to a regulator or other device which delivers controlled sample of air to the indicator assembly to be tested. An axial passage 32 extends from the chamber 24 to the threaded inlet end and a resilient seal or packing 34 is provided at the inlet end of the chamber 24.

The opposite end of the chamber 24, which is designated the outer end is also provided with internal threads 38. The threads 38 have sufficient diameter to allow the indicator tube to be easily inserted into the chamber 24.

A cap 40 has a circular knob 42 with knurling applied about the periphery of the knob. Axially-extended threaded projection 44 may be manually screwed into or out of engagement with the threads 38 at the outer end of the cylindrical housing. An axially extending bore 46 extends through the cap communicating with an enlarged bore 48 at the inner end housing which bore contains a seat 49 of nylon or other elastomeric material. When the cap is secured in place, the adjacent end of the indicator tube will be snugly engaged in the seat 49 with the opposite end of the tube engaging seat 34.

The outer end of the axial passageway 46 terminates at an enlarged recess 50 in the outer surface of the knob. The recess 50 has a diameter which is selected so that the tips 16 and 16A may be easily inserted in the recess and ruptured or broken at the time of use as indicated by FIG. 3. The tube is similar to an ampoule which is frangible and is hermetically sealed and broken at time of use.

FIG. 5 illustrates the replaceable indicator tube in an activated position within the cartridge. Note that both tips 16 and 16A of the tube have been broken off to expose the reagent 11 within the tube so that a controlled sample of air to be tested may be introduced at the distal inlet end of the tube to flow axially through the tube and be discharged through the axial passageway 46 in the cap.

The detection and quantitative determination of carbon monoxide in the air or the gas is achieved by exposing the indicator material to a controlled air sample and analysis can be made quickly by a visual observation of the color change that is imparted to the indicator material. The indicator material of the type described above, when exposed to air containing carbon monoxide, undergoes a color change such as from white or yellow to a sepia brown. The intensity of the color change depends upon the concentration of carbon monoxide, length of time of exposure and temperature during sampling exposure. The indicator material is contained within a tube of uniform diameter. Since the air sample is controlled, the amount of carbon monoxide affects the color change and will impart a color band of a length which is determined by a concentration of CO. To assist the user, suitable reference indicia or calibrations may be provided which may be in the form of a color band reference chart 60 applied to the indicator tube or to the cartridge. The color reference chart has bands of different intensities of the color which results when a color change occurs. The bands each represent different concentration levels of CO. The user can then compare the color intensity imparted to the indicating material with the color chart to amount of carbon monoxide present. The accuracy of the determination of the amount of CO is as much as 1 part in 500,000,000 which is more than adequate.

Alternatively, reference calibrations 62 may be in the form of graduations axially spaced apart on a lens covering the viewing slot 26. The length of the color band caused by the contaminant may be used as an indication of the concentration of the contaminant. The calibrations are selected in accordance with the reagent, size of the indicator tube, sampling flow rate, time and other test parameters.

In addition, the presence of oil in an air sample can be detected as oil will generally be trapped at the inlet end of the replaceable indicator tube at zone 65 in the absorbent carrier material which is typically a silica gel. If excessive oil appears, the user will be alerted to a possible hazard and can take appropriate action.

As mentioned above, the indicator tube can be connected to the air supply to be tested by various mechanical arrangements. In the case of a compressed air tank of the type used by divers, one particularly effective connector assembly is shown in FIG. 1. The scuba tank 70 contains compressed air which is under pressure. Typically a full air tank may contain between 60 and 100 cubic feet of air at pressures of up to 3300 psi. The upper end of the conventional tank is provided with a tank valve 75. The tank and valve assembly typically are of the type available from various well-known manufacturers of scuba equipment. The indicating assembly is temporarily attached to the air supply by means of a yoke 80 which fits about the tank valve 75. The yoke 80 is secured in place by threaded screw 82 which is rotatable at enlarged knob 85. Air is selectively released from the air tank 70 by means of valve control handle 86. Air released through tank valve 75 is introduced into cylindrical fitting 88 which is connected to a regulator 90. The regulator 90 may be any conventional type such as a Victor which provides a predetermined pressure-regulated air supply sample to the indicator assembly 10. The indicator assembly 10 is placed in threaded engagement with the regulator at the inlet end of the tube as indicated in FIGS. 1 and 5. The regulator is shown having suitable pressure gauges 96 and 98 which provide the user an indication of both the tank pressure and the pressure of the supply sample.

In use, indicator tube is prepared for insertion into the cartridge by breaking the opposite ends 16 and 16A off, using the breaker recess in the cap 40. Once the ends of the indicator tube have been broken, the tube is inserted into the cartridge and the cap 40 turned to snugly seat the tube in the cartridge. The connector yoke 80 has been positioned about the tank valve 75 and secured in place by tightening knob 85. A predetermined air sample is admitted into the interior of the indicator tube by opening the air tank valve 75 for a predetermined period of time at handle 86. It has been found that when using the indicator tubes of the type manufactured by Bacharach, that the air sample duration time should be approximately ten seconds. When this time period is over, air valve 75 is turned off and the condition of the indicator tube 12 is viewed at the viewing window. The reference calibrations 62 or color band chart 60 will provide the user a handy reference for determining quantitative amounts of carbon monoxide present. Visual inspection will also alert the user to excessive oil in the air supply. If the visual indication indicates acceptable levels of carbon monoxide, generally below 30 parts per million, the air would then be apparently suitable for use, at least in terms of carbon monoxide levels. The indicator tube is a single-use tube and should be removed and discarded so the unit is ready to accept a new indicator tube for subsequent testing of air.

In FIG. 1, the indicator assembly is shown in a configuration in which the cartridge is internally threaded at the inlet end. In FIG. 6, an alternative coupling arrangement is shown in which the inlet end of the cartridge 20 is provided with a quick-connect coupling 100 which can be suitably engaged with a cooperating member which is part of the regulator 90.

In FIG. 7, the inlet end of the cartridge 20 is shown as having external threads 102 with an annular sealing member 104 extending about the threads. In this configuration, the regulator or other receiving fitting is internally threaded to receive the threaded end of the cartridge.

FIG. 8 shows another embodiment of the invention which is generally designated by the numeral 125. With this embodiment, air indicator tube of the type described above is housed in a cartridge 125. The cartridge 125 has a body 128 which is elongate and generally cylindrical defining an axially extending interior chamber 130 which receives the predeter-indicator tube. The body is preferably a clear or transparent plastic material such as an acrylic which is rigid and resistive to most chemicals, oil, grease and the like. The inlet end 130 of the cartridge is internally threaded at 132 to be attachable to the source of supply air as has been described above. The opposite end of the cartridge is internally threaded adapted to receive cap 135 which has a knob 136 which carries axially extended threaded projection 138. The cap is in threaded engagement with the body to accommodate insertion and removal of the tube.

Because the entire body of the cartridge is clear, the indicator tube when housed in the cartridge is easily viewable by the user. Suitable calibrations in the form of axially spaced annularly extending markings 140 or reference color bands 142 may be placed at appropriate locations along the body of the cartridge.

FIGS. 9 and 10 show still another embodiment of the present invention which is generally designated by the numeral 150. In the embodiment 150 shown in FIGS. 9 and 10, the indicator assembly 10 consisting of the cartridge 20 and tube 12 are as have been described with reference to FIGS. 3 to 5. In this embodiment however, an adaptor unit is provided which when installed in a suitable air line and temporarily receives the indicator assembly while the test is conducted. Preferably, the adaptor which is designated as 152 would be a permanent component of the diving system and, for example, may be installed in an air supply low pressure hose such as the hose leading to the inflation exhaust assembly connected to the buoyancy control.

Referring to the drawings, adaptor 152 has a body 154 which may be any convenient shape but is depicted having side walls 156, 158, front wall 160, rear wall 162, bottom 166 and top 164. A passageway 170 extends vertically from the top wall 164 to the bottom wall 166. The upper end of the passage receives quickconnect/disconnect coupling 180 which is shown connected to a source of air, in this case, a low pressure line 182, connected to the air tank. The opposite end of passageway 170 is internally threaded and connected to a fitting 184 attached to a hose 186 which is connected to the buoyancy control. The adaptor is fabricated of any appropriate material such as plastic or brass and is small and light and may be connected in the manner described above and remain a part of the diver's equipment.

At an intermediate location along passage 170, a threaded bore 172 intersects the passage 170. The threaded bore 172 receives a valve member 190 preferably is a Schrader-type valve having a pin-type actuator 192. When actuator 192 is depressed, air will be diverted through the center of the valve. The Schrader-type valve discharges into a recess 194. Recess 194 houses a spring 196 and actuator button 198. The inner end of the actuator button has a projection 199 which aligns with the actuating pin of the valve. The button is normally urged outwardly by the spring and is manually depressed to divert air from passage 170. The air diverted from passage 170 upon actuation of the valve is delivered to port 200 via passageway 202. Port 200 is internally threaded so that indicator tube assembly may be temporarily secured to the adaptor. The indicator assembly may be of the type as shown in FIGS. 2 to 5 or may be provided with an externally threaded end as shown in FIG. 7.

With the adaptor embodiment shown in FIGS. 9 and 10, the user will assemble the indicator tube assembly as has been described above, first preparing the indicator tube for use by breaking the ends of the tube off and inserting the tube in the cartridge. Once the tube is properly inserted and secured in the cartridge, the cartridge will be screwed into the adaptor at port 200. The actuator button 198 is depressed for a predetermined period of time to deliver a predetermined air sample across the valve and into and through the indicator tube. Upon completion of the test, the indicator tube assembly may be removed from the adaptor and inspected by the user.

FIGS. 11 through 14 show another embodiment of the present invention which is generally designated by the numeral 205. In this embodiment, an adaptor 210 is provided which is quickly and easily connectable to an air source such as a hose leading from the buoyancy control of a diver's vest. The opposite end of the adaptor 210 provides a location for the attachment of a cartridge and indicating tube.

As shown, the adaptor 210 has a body 212 which is generally shown as being a block-like shape but may have any suitable configuration. The body 212 has an axially extending internally threaded bore 214 at one end which connects to reduced diameter threaded bore 216 at its inner end. The reduced diameter threaded bore 216 communicates with an axial chamber 218. The opposite end of chamber 218 is threaded at 222. A threaded male fitting 225 extends from the downstream end of the adaptor. As indicated in FIGS. 13 and 14, the air flow is from the left side of the valve to the right side as viewed in FIG. 11 and is indicated by an air flow arrow. A quick connect fitting 230 is in engagement with threaded bore 214. A suitable O-ring or other sealing member 232 may be provided to minimize leakage around the fitting 230. The fitting 230 is of conventional design and is adapted for easy connection to the source of air to be tested. As shown, the convenient location for attachment to the air source is the hose 240 leading from the buoyancy control of the diver's vest. The hose 240 terminates at a fitting 242 which may be easily connected to fitting 230 of the adaptor.

An air quality indicator 10 of the type previously described may be conveniently attached to the threaded fitting 225 at the downstream end of the adaptor. The indicator 10 has been described previously and includes an external cartridge 20 having threaded section which is engageable with the threaded section 225 of the adaptor. The cartridge is adapted to contain a single use indicator tube 12 containing a suitable indicating substance. When the tube 12 is actuated, as for example by breaking off a tip of the tube or otherwise breaking the seal to allow air to enter the tube, a colorimetric response will be given if certain selected substances are detected.

The adaptor of the present invention allows for quick and convenient attachment to the air source such as at the buoyancy control hose 240. Further, the adaptor provides a controlled rate of air flow to the indicating tube.

The air sample to be tested enters the valve at quick connect fitting 230 and flows through orifice 252 in set screw 250 located in threaded bore 216. The set screw is best seen in FIG. 12. The inner end of the set screw 250 defines a spherical surface 254 which provides a seat for spherical ball 260. The ball 260 operates as a check valve and is biased into engagement with the spherical seat 254 by a spring 262. The opposite end of the spring 262 engages calibrating screw 270. Calibrating screw 270 defines an axially extending aperture 272 to allow air to be tested to flow into the indicating tube. Screw 270 has a diametrically extending groove 275 in its outer end as best seen in FIG. 14. This facilitates initial calibration of the adaptor valve.

Calibration is necessary because of the varying flow requirements of the indicating tubes. Typically, an indicating tube will require a flow of 100 mil per minute. Accordingly, the adaptor is calibrated for the particular requirements of the type of indicating tube 12 to be used and preferably this is pre-set at the factory. Thus the adaptor valve is assembled and placed on a calibration assembly having a regulated air supply. Typically, the buoyancy controls are regulated to provide a predetermined pressure, as for example 18 psi. Therefore, the regulated air supply would be provided at 18 psi and connected to the inlet fitting 230 of the adaptor. A flow meter is connected to the opposite end of the valve at male fitting 225. Readings are taken and calibration screw 270 adjusted in either axial direction until the predetermined flow rate is achieved. For diving applications having low pressure setting and a buoyancy control at 18 psi and using an indicating tube of the type described above, a typical calibrated flow rate setting would be 100 mil per minute. Once the desired setting is achieved, the calibration procedure is preferably continued so that the desired flow rate is maintained for a predetermined period of time, as for example three to four minutes. During calibration, the set screw 270 may be easily adjusted by inserting a tool into diametral groove 275. Once the device is calibrated, the set screw, being an internal component of the device, is not positioned where it normally would be accessed and the setting changed by the user. Also, suitable labeling would be applied to the device cautioning the users not to change the calibration and further indicating that the type of indicating device that is to be used with the adaptor.

The user is provided with the adaptor valve having a quick connect at one end and including a cartridge and replaceable indicating tubes.

The device is convenient and easy to use as the user simply has to insert the appropriate indicating tube within the cartridge 20 and attach the cartridge to the adaptor valve at the outlet end. The inlet end is connected at fitting 230 and the air supply to be tested.

Thus, from the foregoing, it will be seen the present invention provides a convenient, unique and easy-to-use indicator device which is variously attachable to a source of air to be tested. The user can quickly direct the flow of air through the device and the replaceable indicator. The toxic substances will react with the reagent and the indicator indicating the presence of carbon monoxide or other substances.

The device has several embodiments and is easily portable consisting of two primary components, the cartridge and the replaceable chemically reactive indicator tube. A predetermined or fixed air sample is directed to the tube. The chemical component is extremely sensitive and can detect and estimate small amounts of CO as little as 1 part in 500,000,000. This accuracy is more than sufficient to detect CO levels of concern to a diver.

It will be obvious to those skilled in the art to make various changes, alterations and modifications to the device described herein. To the extent these various changes, alterations and modifications do not depart from the spirit and scope of the appended claims, they are intended to be encompassed therein.

We claim:

1. A device for visually determining the presence of a contaminant substance in a compressed air supply contained within a supply tank having a fitting, said device comprising:

(a) an adaptor member having a body with a bore therein having an inlet and an outlet end, said inlet end connectable to said tank fitting, said bore including a screw the inner surface of which defines a semi-spherical seat:

(b) check valve means in the form of a ball engaging said semi-spherical seat and adjustable spring means urging said check valve means into engagement with said semi-spherical seat, wherein said adjustable spring means is adjustable to allow a user to selectively calibrate said check valve means to a predetermined pressure drop at a predetermined gas flow rate through said adaptor member;

(c) an indicating member containing a substance which undergoes a specific visual, observable physical change upon being exposed to a contaminant substance; and (d) a housing for receiving said indicating member, said housing having an inlet end connectable to the outlet end of said adaptor member.

2. The device of claim 1 wherein the air supply is part of the buoyancy controls of an self-contained breathing apparatus system.

3. The device of claim 1 wherein said indicating member comprises a generally elongate transparent tube and said housing defines a generally elongate chamber for receiving said indicating member.

4. The device of claim 3 wherein said transport tube has a frangible section which is broken at the time a test is conducted.

5. The device of claim 1 wherein said indicating member contains a material for detecting carbon monoxide.

6. The device of claim 1 wherein said housing is a generally cylindrical member having a chamber with a seal to receive said indicating member.

* * * * *